(12) United States Patent
Schmidt et al.

(10) Patent No.: US 8,993,249 B2
(45) Date of Patent: Mar. 31, 2015

(54) ANTI-NEUROPILIN ANTIBODIES AND METHODS OF USE

(71) Applicant: Genentech, Inc., South San Francisco, CA (US)

(72) Inventors: Maike Schmidt, San Francisco, CA (US); Christopher Adam Callahan, Belmont, CA (US); Jo-Anne S. Hongo, Redwood City, CA (US); Hartmut Koeppen, San Mateo, CA (US); Ryan J. Watts, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/737,550

(22) Filed: Jan. 9, 2013

(65) Prior Publication Data

US 2013/0115626 A1  May 9, 2013

Related U.S. Application Data

(63) Continuation of application No. PCT/US2011/043318, filed on Jul. 8, 2011.

(60) Provisional application No. 61/363,121, filed on Jul. 9, 2010.

(51) Int. Cl.
| | | |
|---|---|---|
| G01N 33/53 | (2006.01) | |
| C07K 16/00 | (2006.01) | |
| C07K 16/18 | (2006.01) | |
| C07K 16/28 | (2006.01) | |
| A61K 39/395 | (2006.01) | |

(52) U.S. Cl.
CPC .................................. *C07K 16/2863* (2013.01)
USPC .................... 435/7.1; 530/387.1; 530/388.85; 424/130.1; 424/134.1; 424/143.1

(58) Field of Classification Search
None
See application file for complete search history.

(56) References Cited

U.S. PATENT DOCUMENTS

| | | | |
|---|---|---|---|
| 4,675,187 A | 6/1987 | Konishi et al. | |
| 4,816,567 A | 3/1989 | Cabilly et al. | |
| 5,427,908 A | 6/1995 | Dower et al. | |
| 5,432,018 A | 7/1995 | Dower et al. | |
| 5,498,530 A | 3/1996 | Schatz et al. | |
| 5,500,362 A | 3/1996 | Robinson et al. | |
| 5,521,184 A | 5/1996 | Zimmermann | |
| 5,580,717 A | 12/1996 | Dower et al. | |
| 5,658,727 A | 8/1997 | Barbas et al. | |
| 5,723,286 A | 3/1998 | Dower et al. | |
| 5,733,743 A | 3/1998 | Johnson et al. | |
| 5,750,373 A | 5/1998 | Garrard et al. | |
| 5,837,242 A | 11/1998 | Holliger et al. | |
| 5,969,108 A | 10/1999 | McCafferty et al. | |
| 6,172,197 B1 | 1/2001 | McCafferty et al. | |
| 6,204,011 B1 | 3/2001 | Kendall et al. | |
| 6,573,293 B2 | 6/2003 | Tang et al. | |
| 6,727,256 B1 | 4/2004 | Carter et al. | |
| 7,273,612 B2 | 9/2007 | Klagsbrun et al. | |
| 7,335,357 B2 | 2/2008 | Klagsbrun et al. | |
| 7,563,443 B2 | 7/2009 | Grant et al. | |
| 7,638,606 B2 | 12/2009 | Carter et al. | |
| 7,994,286 B2 | 8/2011 | Watts et al. | |
| 8,378,080 B2 | 2/2013 | Watts et al. | |
| 2002/0132774 A1 | 9/2002 | Klagsbrun et al. | |
| 2006/0166878 A1 | 7/2006 | Klagsbrun et al. | |
| 2008/0076906 A1 | 3/2008 | Klagsbrun et al. | |
| 2008/0213268 A1 | 9/2008 | Watts et al. | |

FOREIGN PATENT DOCUMENTS

| | | |
|---|---|---|
| CN | 101326196 A | 12/2008 |
| EP | 0368684 A1 | 5/1990 |
| EP | 0404097 A2 | 12/1990 |
| EP | 0564409 A1 | 10/1993 |
| EP | 0817648 A1 | 1/1998 |
| WO | WO-89/06692 A1 | 7/1989 |
| WO | WO-93/11161 A1 | 6/1993 |
| WO | WO-94/11499 A1 | 5/1994 |
| WO | WO-95/27062 A1 | 10/1995 |
| WO | WO-95/33050 A1 | 12/1995 |
| WO | WO-96/40769 A1 | 12/1996 |
| WO | WO-97/08313 A1 | 3/1997 |
| WO | WO-98/35958 A1 | 8/1998 |
| WO | WO-98/45331 A2 | 10/1998 |
| WO | WO-98/45332 A2 | 10/1998 |
| WO | WO-99/29729 A2 | 6/1999 |
| WO | WO-99/29858 A1 | 6/1999 |
| WO | WO-99/29861 A1 | 6/1999 |
| WO | WO-99/35146 A1 | 7/1999 |
| WO | WO-01/60814 A2 | 8/2001 |
| WO | WO-03/102157 A2 | 12/2003 |
| WO | WO-2004/056874 A2 | 7/2004 |
| WO | WO-2007/056470 A2 | 5/2007 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Commnications. 307:198-205.*
Chen et al. (1999). J. Mol. biol. 293:865-881.*
Wu et al. (1999). J. Mol. Biol. 294:151-162.*
Adamis et al., "Inhibition of vascular endothelial growth factor prevents retinal ischemia-associated iris neovascularization in a nonhuman primate," Arch Ophthalmol. 114(1):66-71 (1996).
Aiello et al., "Vascular endothelial growth factor in ocular fluid of patients with diabetic retinopathy and other retinal disorders," N. Engl J Med. 331(22):1480-7 (1994).

(Continued)

*Primary Examiner* — Christine J Saoud
*Assistant Examiner* — Jon M Lockard
(74) *Attorney, Agent, or Firm* — Clark & Elbing LLP; Karen L. Elbing

(57) ABSTRACT

The invention provides anti-NRP1 antibodies and methods of using the same.

8 Claims, 2 Drawing Sheets

(56) References Cited

OTHER PUBLICATIONS

Amit et al., "Three-dimensional structure of an antigen-antibody complex at 2.8 A resolution," Science. 233(4765):747-53 (1986).
Anonymous, "Anti-neuropilim 1 [EPR3113] antibody (ab81321)," <http://www.abcam.com/neuropilin-1-epr3113-antibody-ab81321.html>, retrieved on Jun. 22, 2010 (9 pages).
Bachelder et al., "Vascular endothelial growth factor is an autocrine survival factor for neuropilin-expressing breast carcinoma cells," Cancer Res. 61(15):5736-40 (2001).
Baluk et al., "Cellular abnormalities of blood vessels as targets in cancer," Curr Opin Genet Dev. 15(1):102-11 (2005).
Barbas et al., "In vitro evolution of a neutralizing human antibody to human immunodeficiency virus type 1 to enhance affinity and broaden strain cross-reactivity," Proc Natl Acad Sci USA. 91(9):3809-13 (1994).
Barbas et al., "Selection and evolution of high-affinity human antiviral antibodies," Trends Biotechnol. 14(7):230-4 (1996).
Basile et al., "Class IV semaphorins promote angiogenesis by stimulating Rho-initiated pathways through plexin-B," Cancer Res. 64(15):5212-24 (2004).
Bendig, "Humanization of rodent monoclonal antibodies by CDR grafting," Methods. 8(2):83-93 (1995).
Benjamin et al., "A plasticity window for blood vessel remodelling is defined by pericyte coverage of the preformed endothelial network and is regulated by PDGF-B and VEGF," Development. 125(9):1591-8 (1998).
Bergers et al., "Benefits of targeting both pericytes and endothelial cells in the tumor vasculature with kinase inhibitors," J Clin Invest. 111(9):1287-95 (2003).
Berkman et al., "Expression of the vascular permeability factor/vascular endothelial growth factor gene in central nervous system neoplasms," J Clin Invest. 91(1):153-9 (1993).
Bielenberg et al., "Neuropilins in neoplasms: expression, regulation, and function," Exp Cell Res. 312(5):584-93 (2006).
Bodey et al., "Failure of cancer vaccines: the significant limitations of this approach to immunotherapy," Anticancer Res. 20(4):2665-76 (2000).
Borgstrom et al., "Complete inhibition of angiogenesis and growth of microtumors by anti-vascular endothelial growth factor neutralizing antibody: novel concepts of angiostatic therapy from intravital videomicroscopy," Cancer Res. 56(17):4032-9 (1996).
Bradbury et al., "Antibodies from phage antibody libraries," J Immunol Methods. 290(1-2):29-49 (2004).
Brown et al., "Expression of vascular permeability factor (vascular endothelial growth factor) and its receptors in adenocarcinomas of the gastrointestinal tract," Cancer Res. 53(19):4727-35 (1993).
Brown et al., "Expression of vascular permeability factor (vascular endothelial growth factor) and its receptors in breast cancer," Hum Pathol. 26(1):86-91 (1995).
Cai et al., "Cloning and characterization of neuropilin-1-interacting protein: a PSD-95/DIg/ZO-1 domain-containing protein that interacts with the cytoplasmic domain of neuropilin-1," J Neurosci. 19(15):6519-27 (1999).
Carmeliet et al., "Angiogenesis in cancer and other diseases," Nature. 407(6801):249-57 (2000).
Carmeliet et al., "Common mechanisms of nerve and blood vessel wiring," Nature. 436(7048):193-200 (2005).
Carter et al., "High level *Escherichia coli* expression and production of a bivalent humanized antibody fragment," Biotechnology (NY). 10(2):163-7 (1992).
Carter et al., "Humanization of an anti-p185HER2 antibody for human cancer therapy," Proc Natl Acad Sci USA. 89(10):4285-9 (1992).
Champe et al., "Monoclonal antibodies that block the activity of leukocyte function-associated antigen 1 recognize three discrete epitopes in the inserted domain of CD11a," J Biol Chem. 270(3):1388-94 (1995).
Chen et al., "Akt1 regulates pathological angiogenesis, vascular maturation and permeability in vivo," Nat Med. 11(11):1188-96 (2005).
Chen et al., "Neuropilin-2, a novel member of the neuropilin family, is a high affinity receptor for the semaphorins Sema E and Sema IV but not Sema III," Neuron. 19(3):547-59 (1997).
Chothia et al., "Canonical structures for the hypervariable regions of immunoglobulins," J Mol Biol. 196(4):901-17 (1987).
Chothia et al., "Conformations of immunoglobulin hypervariable regions," Nature. 342(6252):877-83 (1989).
Clackson et al., "Making antibody fragments using phage display libraries," Nature. 352(6336):624-8 (1991).
Colman, "Effects of amino acid sequence changes on antibody-antigen interactions," Res Immunol. 145(1):33-6 (1994).
Connolly, "Analytical molecular surface calculation," J Appl Crystallogr. 16:548-58 (1983).
Cross et al., "VEGF-receptor signal transduction," Trends Biochem Sci. 28(9):488-94 (2003).
Cunningham et al., "High-resolution epitope mapping of hGH-receptor interactions by alanine-scanning mutagenesis," Science. 244(4908):1081-5 (1989).
de Haard et al., "A large non-immunized human Fab fragment phage library that permits rapid isolation and kinetic analysis of high affinity antibodies," J Biol Chem. 274(26):18218-30 (1999).
De Vries et al., "GIPC, a PDZ domain containing protein, interacts specifically with the C terminus of RGS-GAIP," Proc Natl Acad Sci USA. 95(21):12340-5 (1998).
de Wildt et al., "Antibody arrays for high-throughput screening of antibody-antigen interactions," Nat Biotechnol. 18(9):989-94 (2000).
Deng et al., "Selection of antibody single-chain variable fragments with improved carbohydrate binding by phage display," J Biol Chem. 269(13):9533-8 (1994).
Dermer, "Another anniversary for the war on cancer," Biotechnology. 12(3):320 (1994).
Dickson, "Molecular mechanisms of axon guidance," Science. 298(5600):1959-64 (2002).
Dorrell et al., "Mechanisms of endothelial cell guidance and vascular patterning in the developing mouse retina," Prog Retin Eye Res. 25(3):277-95 (2006).
Dougher et al., "Autophosphorylation of KDR in the kinase domain is required for maximal VEGF-stimulated kinase activity and receptor internalization," Oncogene. 18(8):1619-27 (1999).
Dvorak et al., "Vascular permeability factor/vascular endothelial growth factor, microvascular hyperpermeability, and angiogenesis," Am J Pathol. 146(5):1029-39 (1995).
English Translation of Office Action for Chinese Patent Application No. 201180043301.7, mailed Mar. 5, 2014 (2 pages).
Erber et al., "Combined inhibition of VEGF and PDGF signaling enforces tumor vessel regression by interfering with pericyte-mediated endothelial cell survival mechanisms," FASEB J. 18(2):338-40 (2004).
Examination Report for Australian Patent Application No. 2011274528, dated Feb. 26, 2014 (3 pages).
Ezzell, "Cancer 'vaccines': an idea whose time has come?," Journal of NIH Research. 7:46-9 (1995).
FDA News, "FDA Approves First Angiogenesis Inhibitor to Treat Colorectal Cancer," <http://www.fda.gov/bbs/topics/NEWS/2004/NEW01027.html>, retrieved on Feb. 26, 2004 (2 pages).
Ferrara et al., "Angiogenesis as a therapeutic target," Nature. 438(7070):967-74 (2005).
Ferrara et al., "Clinical applications of angiogenic growth factors and their inhibitors," Nat Med. 5(12):1359-64 (1999).
Ferrara et al., "The biology of vascular endothelial growth factor," Endocr Rev. 18(1):4-25 (1997).
Finkle et al., "HER2-targeted therapy reduces incidence and progression of midlife mammary tumors in female murine mammary tumor virus huHER2-transgenic mice," Clin Cancer Res. 10(7):2499-511 (2004).
Folkman et al., "Angiogenesis," J Biol Chem. 267(16):10931-4 (1992).
Folkman et al., "Induction of angiogenesis during the transition from hyperplasia to neoplasia," Nature. 339(6219):58-61 (1989).
Folkman, "Angiogenesis in cancer, vascular, rheumatoid and other disease," Nat Med. 1(1):27-31 (1995).

(56) References Cited

OTHER PUBLICATIONS

Forsberg et al., "Identification of framework residues in a secreted recombinant antibody fragment that control production level and localization in *Escherichia coli*," J Biol Chem. 272(19):12430-6 (1997).
Freshney, Introduction. *Culture of Animal Cells: A Manual of Basic Technique*. Alan R. Liss, Inc., 3-4 (1983).
Fujisawa et al., "Receptors for collapsin/semaphorins," Curr Opin Neurobiol. 8(5):587-92 (1998).
Gallop et al., "Applications of combinatorial technologies to drug discovery. 1. Background and peptide combinatorial libraries," J Med Chem. 37(9):1233-51 (1994).
Garner, Vascular Diseases. *Pathobiology of Ocular Disease. A Dynamic Approach*. Garner and Klintworth, 1625-1710 (1994).
Garrard et al., "Selection of an anti-IGF-1 Fab from a Fab phage library created by mutagenesis of multiple CDR loops," Gene. 128(1):103-9 (1993).
Gengrinovitch et al., "Platelet factor-4 inhibits the mitogenic activity of VEGF121 and VEGF165 using several concurrent mechanisms," J Biol Chem. 270(25):15059-65 (1995).
Gerber et al., "Vascular endothelial growth factor induces expression of the antiapoptotic proteins Bcl-2 and A1 in vascular endothelial cells," J Biol Chem. 273(21):13313-6 (1998).
Gerhardt et al., "Neuropilin-1 is required for endothelial tip cell guidance in the developing central nervous system," Dev Dyn. 231(3):503-9 (2004).
Gerhardt et al., "VEGF guides angiogenic sprouting utilizing endothelial tip cell filopodia," J Cell Biol. 161(6):1163-77 (2003).
Goodman et al., "Unified nomenclature for the semaphorins/collapsins," Cell. 97(5):551-2 (1999).
Gray et al., "Neuropilin-1 suppresses tumorigenic properties in a human pancreatic adenocarcinoma cell line lacking neuropilin-1 coreceptors," Cancer Res. 65(9):3664-70 (2005).
Griffiths et al., "Isolation of high affinity human antibodies directly from large synthetic repertoires," EMBO J. 13(14):3245-60 (1994).
Gu et al., "Characterization of neuropilin-1 structural features that confer binding to semaphorin 3A and vascular endothelial growth factor 165," J Biol Chem. 277(20):18069-76 (2002).
Gu et al., "Neuropilin-1 conveys semaphorin and VEGF signaling during neural and cardiovascular development," Dev Cell. 5(1):45-57 (2003).
Gura, "Systems for identifying new drugs are often faulty," Science. 278(5340):1041-2 (1997).
Hanahan, "Signaling vascular morphogenesis and maintenance," Science. 277(5322):48-50 (1997).
Hansel et al., "Expression of neuropilin-1 in high-grade dysplasia, invasive cancer, and metastases of the human gastrointestinal tract," Am J Surg Pathol. 28(3):347-56 (2004).
Hawkins et al., "Selection of phage antibodies by binding affinity. Mimicking affinity maturation," J Mol Biol. 226(3):889-96 (1992).
He et al., "Neuropilin is a receptor for the axonal chemorepellent Semaphorin III," Cell. 90(4):739-51 (1997).
Herzog et al., "Differential expression of neuropilin-1 and neuropilin-2 in arteries and veins," Mech Dev. 109(1):115-9 (2001).
Hogan et al., "Organogenesis: molecular mechanisms of tubulogenesis," Nat Rev Genet. 3(7):513-23 (2002).
Holliger et al., ""Diabodies": small bivalent and bispecific antibody fragments," Proc Natl Acad Sci USA. 90(14):6444-8 (1993).
Hoogenboom et al., "Antibody phage display technology and its applications," Immunotechnology. 4(1):1-20 (1998).
Horak et al., "Angiogenesis, assessed by platelet/endothelial cell adhesion molecule antibodies, as indicator of node metastases and survival in breast cancer," Lancet. 340(8828):1120-4 (1992).
Houck et al., "The vascular endothelial growth factor family: identification of a fourth molecular species and characterization of alternative splicing of RNA," Mol Endocrinol. 5(12):1806-14 (1991).
Huber et al., "Signaling at the growth cone: ligand-receptor complexes and the control of axon growth and guidance," Annu Rev Neurosci. 26:509-63 (2003).

Inai et al., "Inhibition of vascular endothelial growth factor (VEGF) signaling in cancer causes loss of endothelial fenestrations, regression of tumor vessels, and appearance of basement membrane ghost," Am J Pathol. 165(1):35-52 (2004).
International Search Report for International Patent Application No. PCT/US2011/043318, mailed Nov. 2, 2011 (2 pages).
Jaalouk et al., "The original Pathologische Anatomie Leiden-Endothelium monoclonal antibody recognizes a vascular endothelial growth factor binding site within neuropilin-1," Cancer Res. 67(20):9623-9 (2007).
Jackson et al., "In vitro antibody maturation. Improvement of a high affinity, neutralizing antibody against IL-1 beta," J Immunol. 154(7):3310-9 (1995).
Jain et al., "Lessons from phase III clinical trials on anti-VEGF therapy for cancer," Nat Clin Pract Oncol. 3(1):24-40 (2006).
Jia et al., "Characterization of a bicyclic peptide neuropilin-1 (NP-1) antagonist (EG3287) reveals importance of vascular endothelial growth factor exon 8 for NP-1 binding and role of NP-1 in KDR signaling," J Biol Chem. 281(19):13493-502 (2006).
Jones et al., "Replacing the complementarity-determining regions in a human antibody with those from a mouse," Nature. 321(6069):522-5 (1986).
Kabat et al., "Unusual distributions of amino acids in complementarity-determining (hypervariable) segments of heavy and light chains of immunoglobulins and their possible roles in specificity of antibody-combining sites," J Biol Chem. 252(19):6609-16 (1977).
Kamiya et al., "The preserved expression of neuropilin (NRP) 1 contributes to a better prognosis in colon cancer," Oncol Rep. 15(2):369-73 (2006).
Karihaloo et al., "Vascular endothelial growth factor induces branching morphogenesis/tubulogenesis in renal epithelial cells in a neuropilin-dependent fashion," Mol Cell Biol. 25(17):7441-8 (2005).
Kawakami et al., "Developmentally regulated expression of a cell surface protein, neuropilin, in the mouse nervous system," J Neurobiol. 29(1):1-17 (1996).
Kawakami et al., "Neuropilin 1 and neuropilin 2 co-expression is significantly correlated with increased vascularity and poor prognosis in nonsmall cell lung carcinoma," Cancer. 95(10):2196-201 (2002).
Kawasaki et al., "A requirement for neuropilin-1 in embryonic vessel formation," Development. 126(21):4895-902 (1999).
Kerbel et al., "Possible mechanisms of acquired resistance to anti-angiogenic drugs: implications for the use of combination therapy approaches," Cancer Metastasis Rev. 20(1-2):79-86 (2001).
Kim et al., "Inhibition of vascular endothelial growth factor-induced angiogenesis suppresses tumour growth in vivo," Nature. 362(6423):841-4 (1993).
Klagsbrun et al., "Regulators of angiogenesis," Annu Rev Physiol. 53:217-39 (1991).
Klagsbrun et al., "The role of neuropilin in vascular and tumor biology," Adv Exp Med Biol. 515:33-48 (2002).
Klagsbrun et al., "VEGF/VPF: the angiogenesis factor found?," Curr Biol. 3(10):699-702 (1993).
Knappik et al., "Fully synthetic human combinatorial antibody libraries (HuCAL) based on modular consensus frameworks and CDRs randomized with trinucleotides," J Mol Biol. 296(1):57-86 (2000).
Kohler et al., "Continuous cultures of fused cells secreting antibody of predefined specificity," Nature. 256(5517):495-7 (1975).
Kolodkin et al., "Neuropilin is a semaphorin III receptor," Cell. 90(4):753-62 (1997).
Kowanetz et al., "Vascular endothelial growth factor signaling pathways: therapeutic perspective," Clin Cancer Res. 12(17):5018-22 (2006).
Kunkel et al., "Efficient site-directed mutagenesis using uracil-containing DNA," Methods Enzymol. 204:125-39 (1991).
Kunkel, "Rapid and efficient site-specific mutagenesis without phenotypic selection," Proc Natl Acad Sci USA. 82(2):488-95 (1985).
Latil et al., "VEGF overexpression in clinically localized prostate tumors and neuropilin-1 overexpression in metastatic forms," Int J Cancer. 89(2):167-71 (2000).

(56) References Cited

OTHER PUBLICATIONS

Lebre et al., "Rheumatoid arthritis synovium contains two subsets of CD83-DC-LAMP-dendritic cells with distinct cytokine profiles," Am J Pathol. 172(4):940-50 (2008).
Lee et al., "Bivalent antibody phage display mimics natural immunoglobulin," J Immunol Methods. 284(1-2):119-32 (2004).
Lee et al., "High-affinity human antibodies from phage-displayed synthetic Fab libraries with a single framework scaffold," J Mol Biol. 340(5):1073-93 (2004).
Lee et al., "The interpretation of protein structures: estimation of static accessibility," J Mol Biol. 55(3):379-400 (1971).
Leung et al., "Vascular endothelial growth factor is a secreted angiogenic mitogen," Science. 246(4935):1306-9 (1989).
Li et al., "Pancreatic carcinoma cells express neuropilins and vascular endothelial growth factor, but not vascular endothelial growth factor receptors," Cancer. 101(10):2341-50 (2004).
Liang et al., "Cross-species vascular endothelial growth factor (VEGF)-blocking antibodies completely inhibit the growth of human tumor xenografts and measure the contribution of stromal VEGF," J Biol Chem. 281(2):951-61 (2006).
Liang et al., "Function blocking antibodies to neuropilin-1 generated from a designed human synthetic antibody phage library," J Mol Biol. 366(3):815-29 (2007).
Liu et al., "Upregulation of neuropilin-1 by basic fibroblast growth factor enhances vascular smooth muscle cell migration in response to VEGF," Cytokine. 32(5):206-12 (2005).
Lopez et al., "Transdifferentiated retinal pigment epithelial cells are immunoreactive for vascular endothelial growth factor in surgically excised age-related macular degeneration-related choroidal neovascular membranes," Invest Ophthalmol Vis Sci. 37(5):855-68 (1996).
Lowman et al., "Monovalent phage display: a method for selecting variant proteins from random libraries," Methods. 3(3):205-16 (1991).
Lubarsky et al., "Tube morphogenesis: making and shaping biological tubes," Cell. 112(1):19-28 (2003).
Macchiarini et al., "Relation of neovascularisation to metastasis of non-small-cell lung cancer," Lancet. 340(8812):145-6 (1992).
Marks et al., "By-passing immunization. Human antibodies from V-gene libraries displayed on phage," J Mol Biol. 222(3):581-97 (1991).
Mattern et al., "Association of vascular endothelial growth factor expression with intratumoral microvessel density and tumour cell proliferation in human epidermoid lung carcinoma," Br J Cancer. 73(7):931-4 (1996).
Matthies et al., "Neuropilin-1 participates in wound angiogenesis," Am J Pathol. 160(1):289-96 (2002).
Melnyk et al., "Vascular endothelial growth factor promotes tumor dissemination by a mechanism distinct from its effect on primary tumor growth," Cancer Res. 56(4):921-4 (1996).
Mian et al., "Structure, function and properties of antibody binding sites," J Mol Biol. 217(1):133-51 (1991).
Miao et al., "Neuropilin-1 expression by tumor cells promotes tumor angiogenesis and progression," FASEB J. 14(15):2532-9 (2000).
Miao et al., "Neuropilin-1 mediates collapsin-1/semaphorin III inhibition of endothelial cell motility: functional competition of collapsin-1 and vascular endothelial growth factor-165," J Cell Biol. 146(1):233-41 (1999).
Miller, "Issues and challenges for antiangiogenic therapies," Breast Cancer Res Treat. 75(suppl 1):S45-50 (2002).
Morrison et al., "Chimeric human antibody molecules: mouse antigen-binding domains with human constant region domains," Proc Natl Acad Sci USA. 81(21):6851-5 (1984).
Muller et al., "Novel gene families involved in neural pathfinding," Curr Opin Genet Dev. 6(4):469-74 (1996).
Murga et al., "Neuropilin-1 regulates attachment in human endothelial cells independently of vascular endothelial growth factor receptor-2," Blood. 105(5):1992-9 (2005).

Nakatsu et al., "Angiogenic sprouting and capillary lumen formation modeled by human umbilical vein endothelial cells (HUVEC) in fibrin gels: the role of fibroblasts and Angiopoietin-1," Microvasc Res. 66(2):102-12 (2003).
Nasarre et al., "Semaphorin SEMA3F and VEGF have opposing effects on cell attachment and spreading," Neoplasia. 5(1):83-92 (2003).
Nasarre et al., "Semaphorin SEMA3F has a repulsing activity on breast cancer cells and inhibits E-cadherin-mediated cell adhesion," Neoplasia. 7(2):180-9 (2005).
Neufeld et al., "Semaphorins in cancer," Front Biosci. 10:751-60 (2005).
Ngo et al., Computational Complexity, Protein Structure Prediction, and the Levinthal Paradox. *The Protein Folding Problem and Tertiary Structure Prediction.* Merz and and Le Grand, 492-495 (1994).
Nicolaou et al., "Calicheamicin θ1 : a rationally designed molecule with extremely potent and selective DNA cleaving properties and apoptosis inducing activity," Angew Chem Intl Ed Engl. 33(2):183-6 (1994).
Oh et al., "Selective induction of neuropilin-1 by vascular endothelial growth factor (VEGF): a mechanism contributing to VEGF-induced angiogenesis," Proc Natl Acad Sci USA. 99(1):383-8 (2002).
Omura et al., "Identification of a 190-kDa vascular endothelial growth factor 165 cell surface binding protein on a human glioma cell line," J Biol Chem. 272(37):23317-22 (1997).
Pacios et al., "Arvomol/Contour: molecule surface areas and volumes on personal computers," Computers Chem. 18(4):377-85 (1994).
Pan et al., "Blocking neuropilin-1 function has an additive effect with anti-VEGF to inhibit tumor growth," Cancer Cell. 11(1):53-67 (2007).
Paul, Structure and Function of Immunoglobulins. *Fundamental Immunology.* Raven Press Ltd., 292-295 (1993).
Poltorak et al., "VEGF145, a secreted vascular endothelial growth factor isoform that binds to extracellular matrix," J Biol Chem. 272(11):7151-8 (1997).
Pozas et al., "Age-dependent effects of secreted Semaphorins 3A, 3F, and 3E on developing hippocampal axons: in vitro effects and phenotype of Semaphorin 3A (−/−) mice," Mol Cell Neurosci. 18(1):26-43 (2001).
Presta et al., "Humanization of an anti-vascular endothelial growth factor monoclonal antibody for the therapy of solid tumors and other disorders," Cancer Res. 57(20):4593-9 (1997).
Presta, "Antibody Engineering," Curr Opin Struct Biol. 2:593-6 (1992).
Raper, "Semaphorins and their receptors in vertebrates and invertebrates," Curr Opin Neurobiol. 10(1):88-94 (2000).
Riechmann et al., "Reshaping human antibodies for therapy," Nature. 332(6162):323-7 (1988).
Rossignol et al., "Genomic organization of human neuropilin-1 and neuropilin-2 genes: identification and distribution of splice variants and soluble isoforms," Genomics. 70(2):211-22 (2000).
Rousseau et al., "p38 MAP kinase activation by vascular endothelial growth factor mediates actin reorganization and cell migration in human endothelial cells," Oncogene. 15(18):2169-77 (1997).
Rudikoff et al., "Single amino acid substitution altering antigen-binding specificity," Proc Natl Acad Sci USA. 79(6):1979-83 (1982).
Sato, "Molecular diagnosis of tumor angiogenesis and anti-angiogenic cancer therapy," Int J Clin Oncol. 8(4):200-6 (2003).
Search Report for Chinese Patent Application No. 201180043301.7, dated Feb. 20, 2014 (2 pages).
Serini et al., "Class 3 semaphorins control vascular morphogenesis by inhibiting integrin function," Nature. 424(6947):391-7 (2003).
Sheets et al., "Efficient construction of a large nonimmune phage antibody library: the production of high-affinity human single-chain antibodies to protein antigens," Proc Natl Acad Sci USA. 95(11):6157-62 (1998).
Shojaei et al., "Antiangiogenesis to treat cancer and intraocular neovascular disorders," Lab Invest. 87(3):227-30 (2007).
Sidhu et al., "Phage-displayed antibody libraries of synthetic heavy chain complementarity determining regions," J Mol Biol. 338(2):299-310 (2004).
Six et al., "Akt signaling mediates VEGF/VPF vascular permeability in vivo," FEBS Lett. 532(1-2):67-9 (2002).

(56) References Cited

OTHER PUBLICATIONS

Skerra et al., "Assembly of a functional immunoglobulin Fv fragment in *Escherichia coli*," Science. 240(4855):1038-41 (1988).

Smith, "Filamentous fusion phage: novel expression vectors that display cloned antigens on the virion surface," Science. 228(4705):1315-7 (1985).

Soker et al., "Characterization of novel vascular endothelial growth factor (VEGF) receptors on tumor cells that bind VEGF165 via its exon 7-encoded domain," J Biol Chem. 271(10):5761-7 (1996).

Soker et al., "Inhibition of vascular endothelial growth factor (VEGF)-induced endothelial cell proliferation by a peptide corresponding to the exon 7-encoded domain of VEGF165," J Biol Chem. 272(50):31582-8 (1997).

Soker et al., "Neuropilin-1 is expressed by endothelial and tumor cells as an isoform-specific receptor for vascular endothelial growth factor," Cell. 92(6):735-45 (1998).

Soker et al., "VEGF165 mediates formation of complexes containing VEGFR-2 and neuropilin-1 that enhance VEGF165-receptor binding," J Cell Biochem. 85(2):357-68 (2002).

Spitler, "Cancer vaccines: the interferon analogy," Cancer Biother. 10(1):1-3 (1995).

Stephenson et al., "Neuropilin-1 is differentially expressed in myoepithelial cells and vascular smooth muscle cells in preneoplastic and neoplastic human breast: a possible marker for the progression of breast cancer," Int J Cancer. 101(5):409-14 (2002).

Streit et al., "Angiogenesis, lymphangiogenesis, and melanoma metastasis," Oncogene. 22(20):3172-9 (2003).

Takagi et al., "Expression of a cell adhesion molecule, neuropilin, in the developing chick nervous system," Dev Biol. 170(1):207-22 (1995).

Takagi et al., "The A5 antigen, a candidate for the neuronal recognition molecule, has homologies to complement components and coagulation factors," Neuron. 7(2):295-307 (1991).

Takahashi et al., "A single autophosphorylation site on KDR/Flk-1 is essential for VEGF-A-dependent activation of PLC-gamma and DNA synthesis in vascular endothelial cells," EMBO J. 20(11):2768-78 (2001).

Takahashi et al., "VEGF activates protein kinase C-dependent, but Ras-independent Raf-MEK-MAP kinase pathway for DNA synthesis in primary endothelial cells," Oncogene. 18(13):2221-30 (1999).

Takashima et al., "Targeting of both mouse neuropilin-1 and neuropilin-2 genes severely impairs developmental yolk sac and embryonic angiogenesis," Proc Natl Acad Sci USA. 99(6):3657-62 (2002).

Tonini et al., "Molecular basis of angiogenesis and cancer," Oncogene. 22(42):6549-56 (2003).

Tordjman et al., "A neuronal receptor, neuropilin-1, is essential for the initiation of the primary immune response," Nat Immunol. 3(5):477-82 (2002).

Ulrich et al., "Expression studies of catalytic antibodies," Proc Natl Acad Sci USA. 92(25):11907-11 (1995).

Vanveldhuizen et al., "Differential expression of neuropilin-1 in malignant and benign prostatic stromal tissue," Oncol Rep. 10(5):1067-71 (2003).

Vaughan et al., "Human antibodies with sub-nanomolar affinities isolated from a large non-immunized phage display library," Nat Biotechnol. 14(3):309-14 (1996).

Verhoeyen et al., "Reshaping human antibodies: grafting an antilysozyme activity," Science. 239(4847):1534-6 (1988).

Wang et al., "C terminus of RGS-GAIP-interacting protein conveys neuropilin-1-mediated signaling during angiogenesis," FASEB J. 20(9):E732-41, 1513-17 (2006).

Wang et al., "Neuropilin-1-mediated vascular permeability factor/vascular endothelial growth factor-dependent endothelial cell migration," J Biol Chem. 278(49):48848-60 (2003).

Warren et al., "Regulation by vascular endothelial growth factor of human colon cancer tumorigenesis in a mouse model of experimental liver metastasis," J Clin Invest. 95(4):1789-97 (1995).

Weidner et al., "Tumor angiogenesis and metastasis—correlation in invasive breast carcinoma," N Engl Med. 324(1):1-8 (1991).

Wells et al., "Rapid evolution of peptide and protein binding properties in vitro," Curr Opin Biotechnol. 3(4):355-62 (1992).

Wey et al., "Overexpression of neuropilin-1 promotes constitutive MAPK signalling and chemoresistance in pancreatic cancer cells," Br J Cancer. 93(2):233-41 (2005).

Wu et al., "Length distribution of CDRH3 in antibodies," Proteins. 16(1):1-7 (1993).

Xu et al., "Diversity in the CDR3 region of V(H) is sufficient for most antibody specificities," Immunity. 13(1):37-45 (2000).

Yamada et al., "Exogenous clustered neuropilin 1 enhances vasculogenesis and angiogenesis," Blood. 97(6):1671-8 (2001).

Yelton et al., "Affinity maturation of the BR96 anti-carcinoma antibody by codon-based mutagenesis," J Immunol. 155(4):1994-2004 (1995).

Yuan et al., "Abnormal lymphatic vessel development in neuropilin 2 mutant mice," Development. 129(20):4797-806 (2002).

Zapata et al., "Engineering linear F(ab')2 fragments for efficient production in *Escherichia coli* and enhanced antiproliferative activity," Protein Eng. 8(10):1057-62 (1995).

Zhang et al., "Vascular endothelial growth factor regulates myeloid cell leukemia-1 expression through neuropilin-1-dependent activation of c-MET signaling in human prostate cancer cells," Mol Cancer. 9(1):9 (2010).

* cited by examiner

SEQUENCE LISTING

<160> NUMBER OF SEQ ID NOS: 10

<210> SEQ ID NO 1
<211> LENGTH: 441
<212> TYPE: PRT
<213> ORGANISM: Oryctolagus cuniculus

<400> SEQUENCE: 1

```
Gln Leu Val Glu Glu Ser Gly Gly Gly Leu Val Thr Pro Gly Gly
  1               5                  10                  15

Thr Leu Thr Leu Thr Cys Thr Ala Ser Gly Phe Thr Ile Ser Asn
                 20                  25                  30

Tyr His Met Ser Trp Val Arg Gln Ala Pro Gly Lys Gly Leu Glu
                 35                  40                  45

Trp Ile Gly Ile Ile Tyr Ala Val Ser Ala Ala Thr Trp Ser Ala
                 50                  55                  60

Thr Trp Val Lys Gly Arg Phe Thr Ile Ser Lys Thr Leu Thr Thr
                 65                  70                  75

Val Asp Leu Lys Met Thr Ser Leu Thr Ala Ala Asp Thr Ala Thr
                 80                  85                  90

Tyr Phe Cys Ala Arg Val Arg Ala Pro Gly Asp Ser Thr Tyr Tyr
                 95                 100                 105

Asp Leu Trp Gly Pro Gly Thr Leu Val Thr Val Ser Ser Gly Gln
                110                 115                 120

Pro Lys Ala Pro Ser Val Phe Pro Leu Ala Pro Cys Cys Gly Asp
                125                 130                 135

Thr Pro Ser Ser Thr Val Thr Leu Gly Cys Leu Val Lys Gly Tyr
                140                 145                 150

Leu Pro Glu Pro Val Thr Val Thr Trp Asn Ser Gly Thr Leu Thr
                155                 160                 165

Asn Gly Val Arg Thr Phe Pro Ser Val Arg Gln Ser Ser Gly Leu
                170                 175                 180

Tyr Ser Leu Ser Ser Val Val Ser Val Thr Ser Ser Ser Gln Pro
                185                 190                 195

Val Thr Cys Asn Val Ala His Pro Ala Thr Asn Thr Lys Val Asp
                200                 205                 210

Lys Thr Val Ala Pro Ser Thr Cys Ser Lys Pro Thr Cys Pro Pro
                215                 220                 225

Pro Glu Leu Leu Gly Gly Pro Ser Val Phe Ile Phe Pro Pro Lys
                230                 235                 240

Pro Lys Asp Thr Leu Met Ile Ser Arg Thr Pro Glu Val Thr Cys
                245                 250                 255

Val Val Val Asp Val Ser Gln Asp Asp Pro Glu Val Gln Phe Thr
                260                 265                 270

Trp Tyr Ile Asn Asn Glu Gln Val Arg Thr Ala Arg Pro Pro Leu
                275                 280                 285

Arg Glu Gln Gln Phe Asn Ser Thr Ile Arg Val Val Ser Thr Leu
                290                 295                 300

Pro Ile Ala His Gln Asp Trp Leu Arg Gly Lys Glu Phe Lys Cys
                305                 310                 315

Lys Val His Asn Lys Ala Leu Pro Ala Pro Ile Glu Lys Thr Ile
                320                 325                 330

Ser Lys Ala Arg Gly Gln Pro Leu Glu Pro Lys Val Tyr Thr Met
                335                 340                 345
```

Gly Pro Pro Arg Glu Glu Leu Ser Ser Arg Ser Val Ser Leu Thr
            350                 355                 360

Cys Met Ile Asn Gly Phe Tyr Pro Ser Asp Ile Ser Val Glu Trp
            365                 370                 375

Glu Lys Asn Gly Lys Ala Glu Asp Asn Tyr Lys Thr Thr Pro Ala
            380                 385                 390

Val Leu Asp Ser Asp Gly Ser Tyr Phe Leu Tyr Ser Lys Leu Ser
            395                 400                 405

Val Pro Thr Ser Glu Trp Gln Arg Gly Asp Val Phe Thr Cys Ser
            410                 415                 420

Val Met His Glu Ala Leu His Asn His Tyr Thr Gln Lys Ser Ile
            425                 430                 435

Ser Arg Ser Pro Gly Lys
            440

<210> SEQ ID NO 2
<211> LENGTH: 118
<212> TYPE: PRT
<213> ORGANISM: Oryctolagus cuniculus

<400> SEQUENCE: 2

Gln Leu Val Glu Glu Ser Gly Gly Gly Leu Val Thr Pro Gly Gly
 1               5                  10                  15

Thr Leu Thr Leu Thr Cys Thr Ala Ser Gly Phe Thr Ile Ser Asn
                20                  25                  30

Tyr His Met Ser Trp Val Arg Gln Ala Pro Gly Lys Gly Leu Glu
                35                  40                  45

Trp Ile Gly Ile Ile Tyr Ala Val Ser Ala Ala Thr Trp Ser Ala
                50                  55                  60

Thr Trp Val Lys Gly Arg Phe Thr Ile Ser Lys Thr Leu Thr Thr
                65                  70                  75

Val Asp Leu Lys Met Thr Ser Leu Thr Ala Ala Asp Thr Ala Thr
                80                  85                  90

Tyr Phe Cys Ala Arg Val Arg Ala Pro Gly Asp Ser Thr Tyr Tyr
                95                  100                 105

Asp Leu Trp Gly Pro Gly Thr Leu Val Thr Val Ser Ser
                110                 115

<210> SEQ ID NO 3
<211> LENGTH: 5
<212> TYPE: PRT
<213> ORGANISM: Oryctolagus cuniculus

<400> SEQUENCE: 3

Asn Tyr His Met Ser
 1               5

<210> SEQ ID NO 4
<211> LENGTH: 16
<212> TYPE: PRT
<213> ORGANISM: Oryctolagus cuniculus

<400> SEQUENCE: 4

Ile Ile Tyr Ala Val Ser Ala Ala Thr Trp Ser Thr Trp Val Lys
 1               5                  10                  15

Gly

<210> SEQ ID NO 5

-continued

```
<211> LENGTH: 12
<212> TYPE: PRT
<213> ORGANISM: Oryctolagus cuniculus

<400> SEQUENCE: 5

Val Arg Ala Pro Gly Asp Ser Thr Tyr Tyr Asp Leu
 1               5                  10

<210> SEQ ID NO 6
<211> LENGTH: 216
<212> TYPE: PRT
<213> ORGANISM: Oryctolagus cuniculus

<400> SEQUENCE: 6

Ala Val Val Met Thr Gln Thr Ala Ser Pro Val Ser Ala Val Val
 1               5                  10                  15

Gly Gly Thr Val Thr Ile Asn Cys Gln Ala Ser Gln Thr Ile Ser
                20                  25                  30

Asn Asn Trp Leu Ser Trp Tyr Gln Gln Lys Pro Gly Gln Pro Pro
                35                  40                  45

Lys Leu Leu Ile Tyr Lys Ala Ser Ile Leu Ala Ser Gly Val Pro
                50                  55                  60

Ser Arg Phe Ser Gly Ser Gly Ser Gly Thr Glu Phe Thr Leu Thr
                65                  70                  75

Ile Ser Gly Val Gln Cys Asp Asp Ala Ala Thr Tyr Tyr Cys Leu
                80                  85                  90

Tyr Gly His Tyr Ile Thr Thr Ser Ala His Asn Ala Phe Gly Gly
                95                 100                 105

Gly Thr Glu Val Val Val Lys Gly Asp Pro Val Ala Pro Thr Val
               110                 115                 120

Leu Ile Phe Pro Pro Ala Ala Asp Gln Val Ala Thr Gly Thr Val
               125                 130                 135

Thr Ile Val Cys Val Ala Asn Lys Tyr Phe Pro Asp Val Thr Val
               140                 145                 150

Thr Trp Glu Val Asp Gly Thr Thr Gln Thr Thr Gly Ile Glu Asn
               155                 160                 165

Ser Lys Thr Pro Gln Asn Ser Ala Asp Cys Thr Tyr Asn Leu Ser
               170                 175                 180

Ser Thr Leu Thr Leu Thr Ser Thr Gln Tyr Asn Ser His Lys Glu
               185                 190                 195

Tyr Thr Cys Lys Val Thr Gln Gly Thr Thr Ser Val Val Gln Ser
               200                 205                 210

Phe Asn Arg Gly Asp Cys
               215

<210> SEQ ID NO 7
<211> LENGTH: 114
<212> TYPE: PRT
<213> ORGANISM: Oryctolagus cuniculus

<400> SEQUENCE: 7

Ala Val Val Met Thr Gln Thr Ala Ser Pro Val Ser Ala Val Val
 1               5                  10                  15

Gly Gly Thr Val Thr Ile Asn Cys Gln Ala Ser Gln Thr Ile Ser
                20                  25                  30

Asn Asn Trp Leu Ser Trp Tyr Gln Gln Lys Pro Gly Gln Pro Pro
                35                  40                  45
```

```
Lys Leu Leu Ile Tyr Lys Ala Ser Ile Leu Ala Ser Gly Val Pro
                50                  55                  60

Ser Arg Phe Ser Gly Ser Gly Ser Gly Thr Glu Phe Thr Leu Thr
            65                  70                  75

Ile Ser Gly Val Gln Cys Asp Asp Ala Ala Thr Tyr Tyr Cys Leu
            80                  85                  90

Tyr Gly His Tyr Ile Thr Thr Ser Ala His Asn Ala Phe Gly Gly
            95                  100                 105

Gly Thr Glu Val Val Val Lys Gly Asp
            110

<210> SEQ ID NO 8
<211> LENGTH: 12
<212> TYPE: PRT
<213> ORGANISM: Oryctolagus cuniculus

<400> SEQUENCE: 8

Gln Ala Ser Gln Thr Ile Ser Asn Asn Trp Leu Ser
 1               5                   10

<210> SEQ ID NO 9
<211> LENGTH: 7
<212> TYPE: PRT
<213> ORGANISM: Oryctolagus cuniculus

<400> SEQUENCE: 9

Lys Ala Ser Ile Leu Ala Ser
 1               5

<210> SEQ ID NO 10
<211> LENGTH: 13
<212> TYPE: PRT
<213> ORGANISM: Oryctolagus cuniculus

<400> SEQUENCE: 10

Leu Tyr Gly His Tyr Ile Thr Thr Ser Ala His Asn Ala
 1               5                   10
```

ANTI-NEUROPILIN ANTIBODIES AND METHODS OF USE

RELATED APPLICATIONS

This application is a continuation of International Application No. PCT/US2011/043318 having an international filing date of Jul. 8, 2011, which application claims the benefit of U.S. Provisional Patent Application No. 61/363,121, filed Jul. 9, 2010, the disclosures of which are hereby incorporated by reference in their entireties for all purposes.

SEQUENCE LISTING

The instant application contains a Sequence Listing submitted via EFS-Web and hereby incorporated by reference in its entirety. Said ASCII copy, created on Jan. 8, 2013, is named P4462R1US.txt, and is 9,020 bytes in size.

FIELD OF THE INVENTION

The present invention relates to anti-neuropilin antibodies and methods of using the same.

BACKGROUND

Neuropilin-1 (NRP1) is a multi-functional receptor that contributes to the development of the nervous and vascular systems. NRP1 was initially described as a receptor that binds the semaphorin 3A ligand, acting with plexin co-receptors to regulate axon guidance (He and Tessier-Lavigne, Cell (1997) 90:739-51). It was later shown that NRP1 also binds members of the vascular endothelial growth factor (VEGF) ligand family to mediate vascular development (Soker et al., Cell (1998) 92:735-45; Kawasaki et al., Development (1999) 126:4895-902). In addition, several studies have proposed a role for NRP1 in tumor biology by regulating vascular and/or tumor cell functions (Bielenberg et al., Exp Cell Res (2006) 312: 584-93).

Pan et al., J Biol Chem (2007) 282:24049-56 showed that a monoclonal antibody that binds to NRP1 reduced VEGF-mediated endothelial cell migration in vitro (see also PCT Publication No. WO2007/056470). Blocking VEGF interaction with NRP1 in vivo reduced angiogenesis and vascular remodeling. The anti-NRP1 antibody slowed tumor growth as a single agent; it is proposed that this is due to anti-NRP1 antibody-mediated reduction of vessel sprouting through a VEGF-dependent process. The anti-NRP1 antibody enhanced the anti-angiogenic and anti-tumor effects of VEGF blockade with an anti-VEGF antibody. The data suggest that by reducing vascular remodeling with anti-NRP1, vessels are likely to retain a more immature phenotype. As immature vessels are believed to be more VEGF-dependent, blood vessels in anti-NRP1-treated tumors may be rendered more susceptible to anti-VEGF therapy, thus resulting in combination efficacy in tumor models when combining both therapies (Pan et al., Cancer Cell (2007) 11:53-67). Given the role of NRP1 in angiogenesis, additional tools to detect the presence of NRP1 are desirable.

SUMMARY

The invention provides anti-NRP1 antibodies and methods of using the same. In one embodiment, the invention provides an isolated antibody that binds to neuropilin-1 (NRP1), wherein the antibody comprises (a) HVR-H1 comprising the amino acid sequence of SEQ ID NO:3, (b) HVR-H2 comprising the amino acid sequence of SEQ ID NO:4, and (c) HVR-H3 comprising the amino acid sequence of SEQ ID NO:5. In certain embodiments, the antibody further comprises (a) HVR-L1 comprising the amino acid sequence of SEQ ID NO:8; (b) HVR-L2 comprising the amino acid sequence of SEQ ID NO:9; and (c) HVR-L3 comprising the amino acid sequence of SEQ ID NO:10.

Also provided is an isolated antibody that binds to neuropilin-1 (NRP1), wherein the antibody comprises (a) HVR-L1 comprising the amino acid sequence of SEQ ID NO:8; (b) HVR-L2 comprising the amino acid sequence of SEQ ID NO:9; and (c) HVR-L3 comprising the amino acid sequence of SEQ ID NO:10.

In another embodiment, the invention provides an isolated antibody that binds to neuropilin-1 (NRP1), wherein the antibody comprises (a) a VH sequence having at least 95% sequence identity to the amino acid sequence of SEQ ID NO:2; (b) a VL sequence having at least 95% sequence identity to the amino acid sequence of SEQ ID NO:7; or (c) a VH sequence as in (a) and a VL sequence as in (b). In some embodiments, the antibody comprises a VH sequence of SEQ ID NO:2. In certain embodiments, the antibody comprises a VL sequence of SEQ ID NO:7. Also provided is an isolated antibody that binds to neuropilin-1 (NRP1), wherein the antibody comprises a VH sequence of SEQ ID NO:2 and a VL sequence of SEQ ID NO:7.

In certain embodiments, the antibody of the invention is an IgG1 antibody. In some embodiments the antibody is an antibody fragment that binds neuropilin, e.g., an antibody that lacks an Fc portion, an F(ab')$_2$, an Fab, or an Fv structure. In another aspect the invention provides an immunoconjugate comprising any of the antibodies of the invention.

The invention also provides an isolated nucleic acid encoding any of the anti-NRP1 antibodies of the invention. In one embodiment, a vector comprising the nucleic acid is provided. In one embodiment, a host cell comprising the vector or comprising the nucleic acid is provided. In one embodiment, the host cell is eukaryotic. In one embodiment, the host cell is a CHO cell. In one embodiment, a method of making an anti-NRP1 antibody is provided, wherein the method comprises culturing the host cell under conditions suitable for expression of the nucleic acid encoding the antibody so that the antibody produced. In some embodiments the method further comprises isolating the antibody produced by the methods.

In one aspect, a method of detecting the presence of NRP1 in a biological sample is provided, the method comprising contacting the biological sample with an antibody of the invention under conditions permissive for binding of the antibody to NRP1, and detecting the presence of the bound antibody, e.g., by detecting whether a complex is formed between the antibody and NRP1. Thus, provided herein is an antibody of the invention for use in detecting the presence of NRP1 in a biological sample. In some embodiments, the detection of the presence of NRP1 is by immunohistochemistry.

DETAILED DESCRIPTION OF EMBODIMENTS OF THE INVENTION

I. Definitions

Figure 1:
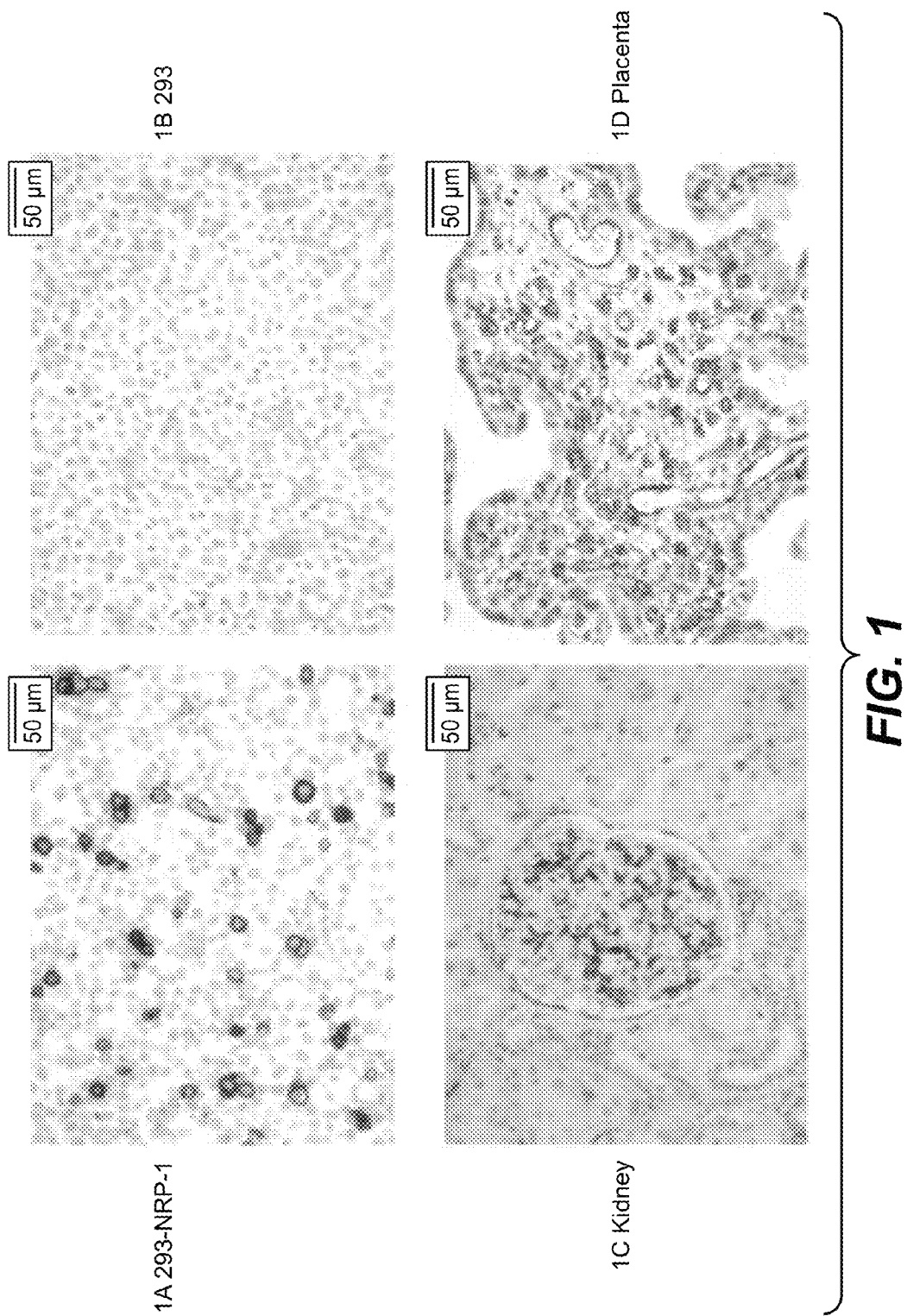
FIG. 1A-D show results of immunohistochemistry using monoclonal anti-NRP1 antibody 7130. (1A: HEK-293 cells transfected with full length human NRP1 (positive control); 1B: HEK-293 cells transfected with empty vector (negative control); 1C: tissue section from kidney; 1D: tissue section from placenta).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-neuropilin-1 antibody," "anti-NRP1 antibody" and "an antibody that binds to NRP1" refer to an antibody that is capable of binding NRP1 with sufficient affinity such that the antibody is useful as a diagnostic and/or therapeutic agent in targeting NRP1. In one embodiment, the extent of binding of an anti-NRP1 antibody to an unrelated, non-NRP1 protein is less than about 10% of the binding of the antibody to NRP1 as measured, e.g., by a radioimmunoassay (RIA). In certain embodiments, an antibody that binds to NRP1 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-NRP1 antibody binds to an epitope of NRP1 that is conserved among NRP1 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. An HVR region as used herein comprise any number of residues located within positions 24-36 (for L1), 46-56 (for L2), 89-97 (for L3), 26-35B (for H1), 47-65 (for H2), and 93-102 (for H3). Therefore, an HVR includes residues in positions described previously:

A) 26-32 (L1), 50-52 (L2), 91-96 (L3), 26-32 (H1), 53-55 (H2), and 96-101 (H3) (Chothia and Lesk, *J. Mol. Biol.* 196: 901-917 (1987);

B) 24-34 of L1, 50-56 of L2, 89-97 of L3, 31-35B of H1, 50-65 of H2, and 95-102 of H3 (Kabat et al., *Sequences of Proteins of Immunological Interest*, 5th Ed. Public Health Service, National Institutes of Health, Bethesda, Md. (1991).

C)) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extra-chromosomally or at a chromosomal location that is different from its natural chromosomal location.

"Isolated nucleic acid encoding an anti-NRP1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "neuropilin-1" or "NRP1," as used herein, refers to any native NRP1 from any vertebrate source, including mammals such as primates (e.g. humans) and rodents (e.g., mice and rats), unless otherwise indicated. The term encompasses "full-length," unprocessed NRP1 as well as any form of NRP1 that results from processing in the cell. The term also encompasses naturally occurring variants of NRP1, e.g., splice variants or allelic variants. The basic structure of neuropilins comprises five domains: three extracellular domains (a1a2, b1b2 and c), a transmembrane domain, and a cytoplasmic domain. The a1a2 domain is homologous to complement components C1r and C1 s (CUB), which generally contains four cysteine residues that form two disculfid bridges. The b1b2 domain is homologous to coagulation factors V and VIII. The central portion of the c domain is designated as MAM due to its homology to meprin, A5 and receptor tyrosine phosphatase µ proteins. The a1a2 and b1b2 domains are responsible for ligand binding, whereas the c domain is critical for homodimerization or heterodimerization. Gu et al. (2002) *J. Biol. Chem.* 277:18069-76; He and Tessier-Lavigne (1997) *Cell* 90:739-51.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

The invention provides novel antibodies that bind to NRP1. Antibodies of the invention are useful, e.g., for detecting the presence of NRP1, for example, in biological samples.

A. Exemplary Anti-NRP1 Antibodies

The invention provides anti-NRP1 antibodies useful for, e.g., diagnostic applications. In one embodiment, the invention provides an anti-NRP1 antibody with the following heavy and light chain sequences:

```
Heavy Chain:
                                              (SEQ ID NO: 1)
QLVEESGGGLVTPGGTLTLTCTASGFTISNYHMSWVRQAPGKGLEWIGIIYAVSAATWSA
                             CDR1                CDR2

TWVKGRFTISKTLTTVDLKMTSLTAADTATYFCARVRAPGDSTYYDLWGPGTLVTVSSGQ
                                   CDR3

PKAPSVFPLAPCCGDTPSSTVTLGCLVKGYLPEPVTVTWNSGTLTNGVRTFPSVRQSSGL

YSLSSVVSVTSSSQPVTCNVAHPATNTKVDKTVAPSTCSKPTCPPPELLGGPSVFIFPPK

PKDTLMISRTPEVTCVVVDVSQDDPEVQFTWYINNEQVRTARPPLREQQFNSTIRVVSTL

PIAHQDWLRGKEFKCKVHNKALPAPIEKTISKARGQPLEPKVYTMGPPREELSSRSVSLT

CMINGFYPSDISVEWEKNGKAEDNYKTTPAVLDSDGSYFLYSKLSVPTSEWQRGDVFTCS

VMHEALHNHYTQKSISRSPGK
```

The amino acid sequence of the heavy chain variable region is the following:

```
                                              (SEQ ID NO: 2)
QLVEESGGGLVTPGGTLTLTCTASGFTISNYHMSWVRQAPGKGLEWIGII

YAVSAATWSATWVKGRFTISKTLTTVDLKMTSLTAADTATYFCARVRAPG

DSTYYDLWGPGTLVTVSS
```

The amino acid sequences of the Kabat CDRs of the heavy chain are the following:

```
                                              (SEQ ID NO: 3)
CDR1: NYHMS;

(SEQ ID NO: 4)
CDR2: IIYAVSAATWSTWVKG;

(SEQ ID NO: 5)
CDR3: VRAPGDSTYYDL.

Light Chain:
                                              (SEQ ID NO: 6)
AVVMTQTASPVSAVVGGTVTINCQASQTISNNWLSWYQQKPGQPPKLLIYKASILASGVP
                      CDR1                       CDR2

SRFSGSGSGTEFTLTISGVQCDDAATYYCLYGHYITTSAHNAFGGGTEVVVKGDPVAPTV
                                 CDR3

LIFPPAADQVATGTVTIVCVANKYFPDVTVTWEVDGTTQTTGIENSKTPQNSADCTYNLS

STLTLTSTQYNSHKEYTCKVTQGTTSVVQSFNRGDC
```

The amino acid sequence of the light chain variable region is the following:

```
                                              (SEQ ID NO: 7)
AVVMTQTASPVSAVVGGTVTINCQASQTISNNWLSWYQQKPGQPPKLLIY

KASILASGVPSRFSGSGSGTEFTLTISGVQCDDAATYYCLYGHYITTSAH

NAFGGGTEVVVKGD
```

The amino acid sequences of the Kabat CDRs of the light chain are the following:

```
                                              (SEQ ID NO: 8)
CDR1: QASQTISNNWLS;

(SEQ ID NO: 9)
CDR2: KASILAS;

(SEQ ID NO: 10)
CDR3: LYGHYITTSAHNA.
```

In one aspect, the invention provides an anti-NRP1 antibody comprising at least one, two, three, four, five, or six HVRs selected from (a) HVR-H1 comprising the amino acid sequence of SEQ ID NO:3; (b) HVR-H2 comprising the amino acid sequence of SEQ ID NO:4; (c) HVR-H3 comprising the amino acid sequence of SEQ ID NO:5; (d) HVR-L1 comprising the amino acid sequence of SEQ ID NO:8; (e) HVR-L2 comprising the amino acid sequence of SEQ ID NO:9; and (f) HVR-L3 comprising the amino acid sequence of SEQ ID NO:10.

In one aspect, the invention provides an antibody comprising at least one, at least two, or all three VH HVR sequences selected from (a) HVR-H1 comprising the amino acid sequence of SEQ ID NO:3; (b) HVR-H2 comprising the amino acid sequence of SEQ ID NO:4; and (c) HVR-H3 comprising the amino acid sequence of SEQ ID NO:5. In one embodiment, the antibody comprises HVR-H3 comprising the amino acid sequence of SEQ ID NO:5. In another embodiment, the antibody comprises HVR-H3 comprising the amino acid sequence of SEQ ID NO:3 and HVR-L3 comprising the amino acid sequence of SEQ ID NO:10. In a further embodiment, the antibody comprises (a) HVR-H1 comprising the amino acid sequence of SEQ ID NO:3; (b) HVR-H2 comprising the amino acid sequence of SEQ ID NO:4; and (c) HVR-H3 comprising the amino acid sequence of SEQ ID NO:5.

In another aspect, the invention provides an antibody comprising at least one, at least two, or all three VL HVR sequences selected from (a) HVR-L1 comprising the amino acid sequence of SEQ ID NO:8; (b) HVR-L2 comprising the amino acid sequence of SEQ ID NO:9; and (c) HVR-L3 comprising the amino acid sequence of SEQ ID NO:10. In one embodiment, the antibody comprises (a) HVR-L1 comprising the amino acid sequence of SEQ ID NO:8; (b) HVR-L2 comprising the amino acid sequence of SEQ ID NO:9; and (c) HVR-L3 comprising the amino acid sequence of SEQ ID NO:10.

In another aspect, an antibody of the invention comprises (a) a VH domain comprising at least one, at least two, or all three VH HVR sequences selected from (i) HVR-H1 comprising the amino acid sequence of SEQ ID NO:3, (ii) HVR-H2 comprising the amino acid sequence of SEQ ID NO:4, and (iii) HVR-H3 comprising an amino acid sequence selected from SEQ ID NO:5; and (b) a VL domain comprising at least one, at least two, or all three VL HVR sequences selected from (i) HVR-L1 comprising the amino acid sequence of SEQ ID NO:8, (ii) HVR-L2 comprising the amino acid sequence of SEQ ID NO:9, and (c) HVR-L3 comprising the amino acid sequence of SEQ ID NO:10.

In another aspect, the invention provides an antibody comprising (a) HVR-H1 comprising the amino acid sequence of SEQ ID NO:3; (b) HVR-H2 comprising the amino acid sequence of SEQ ID NO:4; (c) HVR-H3 comprising the amino acid sequence of SEQ ID NO:5; (d) HVR-L1 comprising the amino acid sequence of SEQ ID NO:8; (e) HVR-L2 comprising the amino acid sequence of SEQ ID NO:9; and (f) HVR-L3 comprising an amino acid sequence selected from SEQ ID NO:10.

In another aspect, an anti-NRP1 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:2. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence (SEQ ID NO:2), but an anti-NRP1 antibody comprising that sequence retains the ability to bind to NRP1. In certain embodiments, a total of 1 to 10 amino acids have been substituted, inserted and/or deleted in SEQ ID NO:2. In certain embodiments, substitutions, insertions, or deletions occur in regions outside the HVRs (i.e., in the FRs). Optionally, the anti-NRP1 antibody comprises the VH sequence in SEQ ID NO:2, including post-translational modifications of that sequence. In a particular embodiment, the VH comprises one, two or three HVRs selected from: (a) HVR-H1 comprising the amino acid sequence of SEQ ID NO:3, (b) HVR-H2 comprising the amino acid sequence of SEQ ID NO:4, and (c) HVR-H3 comprising the amino acid sequence of SEQ ID NO:5.

In another aspect, an anti-NRP1 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:7. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence (SEQ ID NO:7), but an anti-NRP1 antibody comprising that sequence retains the ability to bind to NRP1. In certain embodiments, a total of 1 to 10 amino acids have been substituted, inserted and/or deleted in SEQ ID NO:7. In certain embodiments, the substitutions, insertions, or deletions occur in regions outside the HVRs (i.e., in the FRs). Optionally, the anti-NRP1 antibody comprises the VL sequence in SEQ ID NO:7, including post-translational modifications of that sequence. In a particular embodiment, the VL comprises one, two or three HVRs selected from (a) HVR-L1 comprising the amino acid sequence of SEQ ID NO:8; (b) HVR-L2 comprising the amino acid sequence of SEQ ID NO:9; and (c) HVR-L3 comprising the amino acid sequence of SEQ ID NO:10.

In another aspect, an anti-NRP1 antibody is provided, wherein the antibody comprises a VH as in any of the embodiments provided above, and a VL as in any of the embodiments provided above. In one embodiment, the antibody comprises the VH and VL sequences in SEQ ID NO:2 and SEQ ID NO:7, respectively, including post-translational modifications of those sequences.

In a further aspect, the invention provides an antibody that binds to the same epitope as an anti-NRP1 antibody provided herein. For example, in certain embodiments, an antibody is provided that binds to the same epitope as an anti-NRP1 antibody comprising a VH sequence of SEQ ID NO:2 and a VL sequence of SEQ ID NO:7.

In a further aspect of the invention, an anti-NRP1 antibody according to any of the above embodiments is a monoclonal antibody, including a chimeric, humanized or human antibody. In one embodiment, an anti-NRP1 antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, an anti-NRP1 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20™) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm bandpass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Plückthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J.*

Immunol. 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348: 552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for NRP1 and the other is for any other antigen. In certain embodiments, bispecific antibodies may bind to two different epitopes of NRP1. Bispecific antibodies may also be used to localize cytotoxic agents to cells which express NRP1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to NRP1 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166: 1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/polypropylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-NRP1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-NRP1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-NRP1 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383: 44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

C. Assays

Anti-NRP1 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with any one of the antibodies of the invention for binding to NRP1 (e.g., anti-NRP1 antibody 7130 described below). In certain embodiments, such a competing antibody binds to the same epitope (e.g., a linear or a conformational epitope) that is bound by any one of the antibodies of the invention (e.g., anti-NRP1 antibody 7130 described below). Detailed exemplary methods for mapping an epitope to which an antibody binds are provided in Morris (1996) "Epitope Mapping Protocols," in *Methods in Molecular Biology vol.* 66 (Humana Press, Totowa, N.J.).

In an exemplary competition assay, immobilized NRP1 is incubated in a solution comprising a first labeled antibody that binds to NRP1 (e.g., anti-NRP1 antibody 7130 described below) and a second unlabeled antibody that is being tested for its ability to compete with the first antibody for binding to NRP1. The second antibody may be present in a hybridoma supernatant. As a control, immobilized NRP1 is incubated in a solution comprising the first labeled antibody but not the second unlabeled antibody. After incubation under conditions permissive for binding of the first antibody to NRP1, excess unbound antibody is removed, and the amount of label associated with immobilized NRP1 is measured. If the amount of label associated with immobilized NRP1 is substantially reduced in the test sample relative to the control sample, then that indicates that the second antibody is competing with the first antibody for binding to NRP1. See Harlow and Lane (1988) *Antibodies: A Laboratory Manual ch.* 14 (Cold Spring Harbor Laboratory, Cold Spring Harbor, N.Y.).

2. Detection Assays

In one aspect, assays are provided for identifying anti-NRP1 antibodies useful for detecting the presence of NRP1, e.g., in immunohistochemistry assays. In certain embodiments, an antibody of the invention is tested for such activity.

D. Immunoconjugates

The invention also provides immunoconjugates comprising an anti-NRP1 antibody herein conjugated to one or more agents, such as radioactive isotopes.

In one embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

E. Methods and Compositions for Diagnostics and Detection

In certain embodiments, any of the anti-NRP1 antibodies provided herein is useful for detecting the presence of NRP1 in a biological sample. The term "detecting" as used herein encompasses quantitative or qualitative detection. In certain embodiments, a biological sample comprises a cell or tissue from normal or cancer patients, such as, for example, normal and cancerous tissue of breast, colon, lung, kidney, bone, brain, stomach, pancreas, bladder, ovary, uterus, as well as heart, embryonic and placental tissue.

In one embodiment, an anti-NRP1 antibody for use in a method of diagnosis or detection is provided. In a further aspect, a method of detecting the presence of NRP1 in a biological sample is provided. In certain embodiments, the method comprises contacting the biological sample with an anti-NRP1 antibody as described herein under conditions permissive for binding of the anti-NRP1 antibody to NRP1, and detecting whether a complex is formed between the anti-NRP1 antibody and NRP1. Such method may be an in vitro or in vivo method. In one embodiment, an anti-NRP1 antibody is used to select subjects eligible for therapy with an anti-NRP1 antibody, e.g. where NRP1 is a biomarker for selection of patients.

In certain embodiments, labeled anti-NRP1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^3$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

It is understood that any of the above methods for diagnosis and/or detection may be carried out using an immunoconjugate of the invention in place of or in addition to an anti-NRP1 antibody.

III. EXAMPLES

The following are examples of methods and compositions of the invention. It is understood that various other embodiments may be practiced, given the general description provided above.

Example 1

Generation of Anti-NRP1 Rabbit Monoclonal Antibodies 200 ug human soluble NRP1 antigen was injected into New Zealand white rabbits using 1:1 antigen:complete Freund's Adjuvant, followed by boosting every other week with 100 ug human soluble NRP1 antigen per rabbit. The spleen of one of the rabbits was excised and fused to rabbit myeloma cells using standard techniques. The resulting hybridoma supernatants were screened by ELISA using soluble NRP1 antigen and the positive clones were further screened for reactivity on human embryonic kidney HEK-293 cells transfected with human NRP1 or empty vector (control). Candidate clones were explanded, subcloned by limiting dilution and re-tested by ELISA as above. Monoclonal anti-NRP1 antibody 7130 was obtained and sequenced. The heavy and light chain sequences are the following:

```
Heavy Chain:
                                                        (SEQ ID NO: 1)
QLVEESGGGLVTPGGTLTLTCTASGFTISNYHMSWVRQAPGKGLEWIGIIYAVSAATWSA
                             CDR1                      CDR2

TWVKGRFTISKTLTTVDLKMTSLTAADTATYFCARVRAPGDSTYYDLWGPGTLVTVSSGQ
                                   CDR3

PKAPSVFPLAPCCGDTPSSTVTLGCLVKGYLPEPVTVTWNSGTLTNGVRTFPSVRQSSGL

YSLSSVVSVTSSSQPVTCNVAHPATNTKVDKTVAPSTCSKPTCPPPELLGGPSVFIFPPK

PKDTLMISRTPEVTCVVVDVSQDDPEVQFTWYINNEQVRTARPPLREQQFNSTIRVVSTL

PIAHQDWLRGKEFKCKVHNKALPAPIEKTISKARGQPLEPKVYTMGPPREELSSRSVSLT

CMINGFYPSDISVEWEKNGKAEDNYKTTPAVLDSDGSYFLYSKLSVPTSEWQRGDVFTCS

VMHEALHNHYTQKSISRSPGK

Light Chain:
                                                        (SEQ ID NO: 6)
AVVMTQTASPVSAVVGGTVTINCQASQTISNNWLSWYQQKPGQPPKLLIYKASILASGVP
                       CDR1                         CDR2

SRFSGSGSGTEFTLTISGVQCDDAATYYCLYGHYITTSAHNAFGGGTEVVVKGDPVAPTV
                             CDR3

LIFPPAADQVATGTVTIVCVANKYFPDVTVTWEVDGTTQTTGIENSKTPQNSADCTYNLS

STLTLTSTQYNSHKEYTCKVTQGTTSVVQSFNRGDC
```

Example 2

Immunohistochemistry Using Anti-NRP1 Monoclonal Antibody

Figure 2:
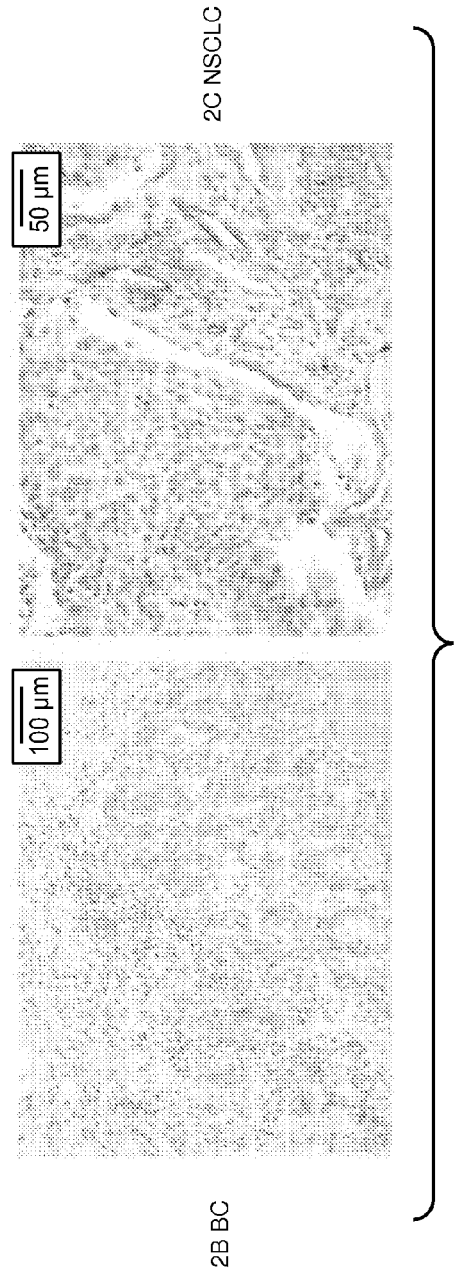
FIG. 2A-C show results of immunohistochemistry using monoclonal anti-NRP1 antibody 7130. (2A: tissue section from colorectal cancer (CRC) patient; 2B: tissue section from breast cancer (BC) patient; 2C: tissue section from non-small cell lung cancer (NSCLC) patient).

Immunohistochemistry (IHC) was performed on freshly cut tissue sections following standard procedure. Tissue sections were incubated with primary antibody (monoclonal anti-NRP1 antibody 7130) at 1 ug/ml followed by standard washes and secondary detection with anti-rabbit biotinylated goat antibody (Vector lab) and Vectastain® ABC-HRP Elite. The specificity of the anti-NRP1 antibody was assessed using HEK-293 cells transfected with human NRP1 and empty vector as control (see FIGS. 1A and 1B). To assess expression, whole sections were scored semi-quantitatively on a scale of zero (no expression) to three (very strong signal), according to the intensity of chromagen deposition in ≥10% of neoplastic cells or endothelium. FIGS. 1C and 1D show IHC of tissue sections from normal kidney and normal placenta, respectively, stained with monoclonal anti-NRP1 antibody 7130. FIG. 2A-C show IHC of tissue sections stained with monoclonal anti-NRP1 antibody 7130 from colorectal cancer, breast cancer and non-small cell lung cancer patients, respectively.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody that binds to neuropilin-1 (NRP1), wherein the antibody comprises a VH sequence of SEQ ID NO:2 and a VL sequence of SEQ ID NO:7.

2. An isolated antibody that binds to neuropilin-1 (NRP1), wherein the antibody comprises (a) HVR-H1 comprising the amino acid sequence of SEQ ID NO:3, (b) HVR-H2 comprising the amino acid sequence of SEQ ID NO:4, (c) HVR-H3 comprising the amino acid sequence of SEQ ID NO:5, (d) HVR-L1 comprising the amino acid sequence of SEQ ID NO:8, (e) HV-L2 comprising the amino acid sequence of SEQ ID NO:9, and (f) HVR-L3 comprising the amino acid sequence of SEQ ID NO:10.

3. The antibody of claim 2, wherein the antibody comprises (a) a VH sequence having at least 95% sequence identity to the amino acid sequence of SEQ ID NO:2 and (b) a VL sequence having at least 95% sequence identity to the amino acid sequence of SEQ ID NO:7.

4. The antibody of claim 2, which is an IgG1 antibody.

5. The antibody of claim 2, which is an antibody fragment that binds neuropilin.

6. An immunoconjugate comprising the antibody of claim 2.

7. A method of detecting the presence of NRP1 in a biological sample comprising contacting the biological sample with the antibody of claim 2 and detecting the presence of the bound antibody.

8. The method of claim 7, wherein the presence of the bound antibody is detected by immunohistochemistry.

* * * * *